United States Patent
Ichihara et al.

(10) Patent No.: US 9,293,886 B2
(45) Date of Patent: Mar. 22, 2016

(54) LASER APPARATUS AND PHOTOACOUSTIC APPARATUS

(75) Inventors: Shigeru Ichihara, Tokyo (JP); Shuichi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 238 days.

(21) Appl. No.: 14/009,561

(22) PCT Filed: Apr. 9, 2012

(86) PCT No.: PCT/JP2012/002463
§ 371 (c)(1),
(2), (4) Date: Oct. 3, 2013

(87) PCT Pub. No.: WO2012/140864
PCT Pub. Date: Oct. 18, 2012

(65) Prior Publication Data
US 2014/0031667 A1    Jan. 30, 2014

(30) Foreign Application Priority Data
Apr. 11, 2011  (JP) .................................. 2011-087696

(51) Int. Cl.
*A61B 5/00*    (2006.01)
*H01S 3/105*    (2006.01)
(Continued)

(52) U.S. Cl.
CPC .............. *H01S 3/105* (2013.01); *A61B 5/0095* (2013.01); *H01S 3/08063* (2013.01); *H01S 3/08068* (2013.01); *H01S 3/08072* (2013.01); *H01S 3/1625* (2013.01); *H01S 3/1636* (2013.01)

(58) Field of Classification Search
CPC ... A61B 5/0095; H01S 3/105; H01S 3/08063; H01S 3/08068; H01S 3/08072; H01S 3/1625; H01S 3/1636
See application file for complete search history.

(56) References Cited

U.S. PATENT DOCUMENTS 5,249,192 A    9/1993    Kuizenga .......................... 372/23
5,840,023 A    11/1998    Oraevsky ....................... 600/407
(Continued)

FOREIGN PATENT DOCUMENTS

JP    H09-162479    6/1997
JP    H11-307859    11/1999
(Continued)

OTHER PUBLICATIONS

JPO Office Action issued on Feb. 24, 2015, in counterpart Japanese patent application 2011-087696, with translation.
(Continued)

*Primary Examiner* — Bo J Peng
(74) *Attorney, Agent, or Firm* — Fitzpatrick, Cella, Harper & Scinto

(57) ABSTRACT

A laser apparatus includes a laser medium; a light source that radiates light to the laser medium, thereby exciting the laser medium and raising the temperature thereof; a reflecting unit having a first plane that reflects light within a predetermined wavelength range from light generated by excitation of the laser medium; and an output mirror disposed opposite the reflecting unit, with the laser medium being interposed therebetween, and causing laser oscillation by inducing resonance of the light within a predetermined wavelength range between the first plane and the output mirror. The reflecting unit is configured to be movable between a position in which light resonance is induced between the output mirror and the first plane and the laser apparatus is set to an oscillation state and a position in which the laser apparatus is set to a non-oscillation state.

13 Claims, 13 Drawing Sheets

(51) Int. Cl.
H01S 3/08 (2006.01)
H01S 3/16 (2006.01)

(56) References Cited

U.S. PATENT DOCUMENTS

| | | | |
|---|---|---|---|
| 7,123,632 B2 | 10/2006 | Wais | 372/15 |
| 8,054,074 B2 | 11/2011 | Ichihara et al. | 324/304 |
| 8,405,389 B2 | 3/2013 | Sugioka et al. | 324/244.1 |
| 2008/0253416 A1 | 10/2008 | Nishikawa et al. | 372/38.01 |
| 2011/0088477 A1 | 4/2011 | Someda et al. | 73/641 |
| 2012/0318066 A1 | 12/2012 | Ichihara et al. | 73/655 |
| 2013/0070802 A1 | 3/2013 | Ichihara | 372/70 |
| 2014/0092932 A1 | 4/2014 | Ichihara | 372/100 |
| 2014/0109678 A1 | 4/2014 | Ichihara | 73/655 |
| 2014/0123762 A1 | 5/2014 | Furukawa et al. | 73/655 |
| 2014/0185634 A1 | 7/2014 | Ichihara et al. | 372/10 |

FOREIGN PATENT DOCUMENTS

| | | |
|---|---|---|
| JP | 2002-094156 | 3/2002 |
| JP | 2008-262976 | 10/2008 |
| JP | 2010-022816 | 2/2010 |

OTHER PUBLICATIONS

S. Manohar et al., "Region-of-Interest Breast Studies Using the Twente Photoacoustic Mammoscope (PAM)", *Proc. of SPIE*, vol. 6437, 6432702 (2007).

C. Wyss et al., "Modulation and Single-Spike Switching of Diode-Pumped $Er^{3+}$:$LiYF_4$ Laser at 2:8 μm", *IEEE Journal of Quantum Electronics*, vol. 34, No. 6, pp. 1041-1045 (Jun. 1998).

Office Action issued Oct. 6, 2015 in counterpart Japanese patent application 2011-087696, with translation.

LASER APPARATUS AND PHOTOACOUSTIC APPARATUS

TECHNICAL FIELD

The present invention relates to a laser apparatus and a photoacoustic apparatus.

BACKGROUND ART

A large number of products using variable wavelength lasers have recently been developed. Lasers have been developed with the object of applications to biochemical measurements and semiconductor measurements in a range from ultraviolet radiation to the visible light and medical measurements in a range from the visible light to near-infrared radiation. Products using specific features of lasers, such as a coherence characteristic and a high-output characteristic, have been developed, but stabilization of laser oscillation at a high output remains to be a basic requirement.

A warm-up process of inducing laser oscillation for several tens of minutes is typically performed to stabilize the laser output. As a result of the warm-up, the temperature of optical members constituting the resonator, a laser medium, an excitation medium, and cooling water is stabilized in a thermal equilibrium state. Patent Literature 1 (PTL 1) discloses a method for determining the laser preparation completion state in which the warm-up process of causing laser oscillation is performed in a stepwise manner and the laser output is stabilized.

In a Nd:YAG laser with flash lamp excitation, a comparatively stable laser output can be obtained by using only light emission from the flash lamp, that is, without causing laser oscillation. The temperature of the Nd:YAG rod disposed adjacently to the lamp rises due to the absorption of energy generated by light emission from the flash lamp, a thermal equilibrium state is attained, and the laser output is stabilized.

Patent Literature 2 (PTL 2) discloses a method for stabilizing laser output by performing temperature control of a KTP crystal, which is a nonlinear optical crystal, by using a Peltier element in a laser generator using the KTP crystal.

A variable wavelength laser with titanium sapphire (Ti:sa) or a dye as a laser medium uses a basic wave of Nd:YAG or the like or a harmonic thereof as an excitation light source and generates laser radiation by causing selective resonance of the wavelength at which the generation is possible. In order to stabilize the generated laser output, it is important to stabilize the laser output of the excitation source and also adjust the temperature of the laser medium (Ti:sa or a dye) to a thermal equilibrium state same as that during laser oscillation.

A Non-Patent Literature 1 (NPL 1) discloses a photoacoustic measurement apparatus as a medical diagnostic apparatus incorporating a variable wavelength laser in which the presence of a tumor inside a breast mass is diagnosed by using a photoacoustic effect. In the photoacoustic measurement apparatus, a measurement site is irradiated with nanosecond pulse laser radiation, ultrasound waves generated in the measurement site are received, and the received signal is analyzed, thereby obtaining an image. By using a wavelength-variable laser such that uses Ti:sa, it is possible to obtain tissue information that is based on the difference in absorption coefficient between the body tissues. Since photoacoustic measurements have a low degree of invasiveness, the measurements can be repeatedly performed, while changing the measurement site. Further, the measurement interval of one cycle is short and the laser generation time is comparatively short. Therefore, laser oscillation is most often induced intermittently and it is important to stabilize the laser output.

CITATION LIST

[Patent Literature]
[PTL 1]
  Japanese Patent Application Publication No. 2008-262976
[PTL 2]
  Japanese Patent Application Publication No. H09-162479
[Non Patent Literature]
  S. Manohar et al., Proc. of SPIE, vol. 6437 (2007) 643702-1

SUMMARY OF INVENTION

Technical Problem

In a variable wavelength laser such as a Ti:sa laser that is used in photoacoustic measurement apparatuses for medical applications, it is preferred that a high and stabilized laser output be obtained regardless of the usage state. The problem encountered when using a laser apparatus that requires the warm-up process such as described in Patent Literature 1 is that the time that should be allocated for a patient in diagnostics is extended and the diagnostic interval is extended. Further, when a high-output laser is used, it is desirable that no laser oscillation be induced prior to diagnostic. Therefore, it is preferred that the conventional warm-up process of inducing laser oscillation be avoided.

FIG. 12 shows a laser resonator 1201 of a Ti:sa laser that has been conventionally used in a variable wavelength mode. A laser medium 1202 constituted by a Ti:sa crystal is excited by excitation light with a wavelength 532 nm, which is a double harmonic of the Nd:YAG laser. A reflecting mirror 1203 is provided at one end side of the laser medium 1202 in the laser resonator 1201. There is also provided an output mirror 1206 that forms together with the reflecting mirror 1203 a resonator structure. A first Brewster dispersing prism 1204 and a second Brewster dispersing prism 1205, which are wavelength selecting elements, are provided between the reflecting mirror 1203 and the laser medium 1202. In the examples shown herein, two dispersing prisms are used.

In FIG. 2, the laser output measured by using the above-described Ti:sa laser is plotted against the ordinate, and time is plotted against the abscissa. In the present measurements, a laser beam with a wavelength of 532 nm, which is the second harmonic of the Nd:YAG laser, is used as the excitation light. Further, the Ti:sa crystal is irradiated in a stabilized state of the excitation light output. As shown in FIG. 2, the output of the Ti:sa laser is low immediately after the irradiation with the excitation light. As the time elapses, the laser output gradually increases and an equilibrium state with the stabilized output is reached. The Ti:sa crystal immediately after the incidence of the excitation light is equal to the surrounding ambient temperature, and the temperature of the Ti:sa crystal is low. As the time of excitation light irradiation elapses, the temperature of the Ti:sa crystal rises. In order to obtain a stable laser output, it is necessary that laser medium be in a thermal equilibrium state. Thus, as the present measurement results show, the problem associated with stabilization of the output of the Ti:sa lasers that have been conventionally used is that a warm-up process is required in which laser oscillation is induced and which takes a certain time.

In order to perform temperature control of the laser medium, a method can be used by which, as described in Patent Literature 2, the temperature of the laser medium is optimized in advance by using a Peltier element or the like.

However, because a sensor for monitoring the temperature and the control mechanism are used, the apparatus configuration is made more complex.

In the conventional configuration shown in FIG. 12, an example is presented in which a Brewster dispersing prism with a comparatively small internal loss is used. However, the drawback of the configuration using a Brewster dispersing prism is that the resonator length increases. As for the wavelength adjustment, the position and angle of the reflecting mirror 1203 are adjusted so as to obtain a resonator structure with respect to an optical path in which light is refracted by two Brewster dispersing prisms. Wavelength selectivity and wavelength resolution vary according to the dispersivity based on the number or refractive indexes of dispersing prisms. Since the position of the reflecting mirror 1203 is determined according to the dispersed wavelength, there is a correlation between the wavelength selection accuracy and positional accuracy of the reflecting mirror 1203. Thus, where dispersing prisms are used, the apparatus is easily increased in size due to the inclusion of the wavelength control mechanism.

A method by which a birefringence filter or a diffraction grating is inserted into the resonator is an example of the conventional approach that does not use the wavelength selection mechanism. However, with such a method, the aforementioned wavelength selective elements have large internal loss, the laser oscillation efficiency decreases, and increase in the output is inhibited.

It is an object of the present invention to resolve the above-described problems and to provide a laser apparatus of a simple configuration that enables stabilization of laser output.

Solution to Problem

The present invention provides a laser apparatus comprising:
a laser medium;
a light source that radiates light to the laser medium, thereby exciting the laser medium and raising a temperature of the laser medium;
a reflecting unit having a first plane that reflects light within a predetermined wavelength range from light generated by excitation of the laser medium; and
an output mirror disposed opposite the reflecting unit, with the laser medium being interposed therebetween, and causing laser oscillation by inducing resonance of the light within a predetermined wavelength range between the first plane and the output mirror, wherein
the reflecting unit is configured to be movable between a position in which light resonance is induced between the output mirror and the first plane and the laser apparatus is set to an oscillation state and a position in which the laser apparatus is set to a non-oscillation state.

Advantageous Effects of Invention

In accordance with the present invention, it is possible to provide a laser apparatus of a simple configuration that enables stabilization of laser output.

Further features of the present invention will become apparent from the following description of exemplary embodiments with reference to the attached drawings.

DESCRIPTION OF EMBODIMENTS

The preferred embodiments of the present invention will be explained below with reference to the appended drawings.

The configuration in accordance with the present invention can be applied to an apparatus using a variable wavelength laser and can be used in various fields, for example, for medical applications.

Figure 1:
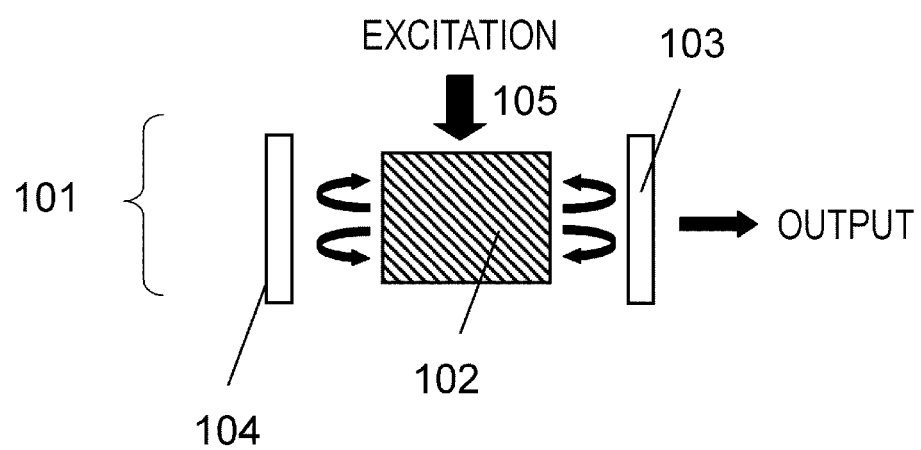
FIG. 1 is a plan view of a basic structure of a laser resonator.
Figure 2:
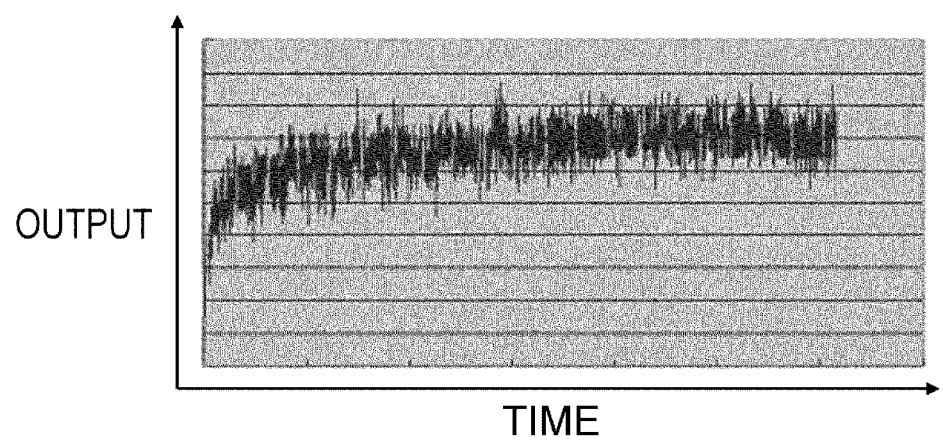
FIG. 2 illustrates the initial oscillation characteristic of a Ti:sa laser.

FIG. 1 shows the basic configuration of a laser resonator 101 of a variable wavelength laser. The resonator 101 is formed by a laser medium 102 and a resonator portion set equivalent to feedback. The resonator portion is constituted by an output mirror 103 that takes out the laser light and a reflecting mirror 104. The laser medium is irradiated by an excitation laser light source according to the absorption characteristic of the laser medium.

By using a laser medium having a gain in a wide wavelength range, such as a dye laser or a titanium sapphire (Ti:sa) laser, it is possible to produce a variable wavelength laser. Examples of the dye include Rhodamine 6G and Coumarin 102, and the oscillation wavelength band differs depending on the dye. The present invention is not limited to a specific dye. Ti:sa is a crystal obtained by doping sapphire with titanium. The Ti:sa laser is a solid state laser capable of oscillating in a wavelength range of 650 nm to 1100 nm. Dyes and Ti:sa are thus laser media with a wide oscillation wavelength region.

A method for stabilizing the laser output in accordance with the present invention will be explained below with reference to a basic condition of laser oscillation.

The basic condition of laser oscillation is that electrons located at the lower level zone are excited to the upper level zone by irradiating the laser medium 102 with the excitation light 105 and population inversion is formed. The gain at the laser medium component is denoted by G and the loss inside the resonator during laser oscillation is denoted by L. The loss inside the resonator as referred to herein is a sum total of a loss on a transmittance of the output mirror 103 relating to the output take-out and an internal loss caused by the optical members located inside the resonator that are other than the output mirror 103.

For the laser light inside the resonator to be amplified and the output to be taken out to the outside of the resonator, the condition of G>L should be fulfilled. Meanwhile, since the number of atoms at the upper level of the laser medium decreases with the increase in the photoelectric field intensity, the gain decreases. Therefore, a balance of the gain and loss is required to obtain stationary laser oscillation. By contrast, when G<L, stationary laser oscillation cannot be obtained.

In accordance with the present invention, a configuration is obtained in which a non-oscillation state can be attained by controlling and increasing the loss (L) inside the resonator, while irradiating the laser medium 102 with the excitation light 105. With such a configuration, the laser medium 102 absorbs the energy of the excitation light 105 and the temperature of the laser medium rises prior to laser oscillation. As a result, it is possible to obtain a laser apparatus in which the temperature of the laser medium can be raised without laser oscillation, a thermal equilibrium state with a stable output can be produced, and the output is stabilized simultaneously with the oscillation.

By providing the reflecting mirror 104 of the laser resonator shown in FIG. 1 with a wavelength selection mechanism, it is possible to construct a variable wavelength laser of a simple configuration. A dielectric reflecting film that reflects the wavelength within a predetermined range is formed on the reflecting mirror 104 as a wavelength selection mechanism. Wavelength selection can be performed by moving the reflecting mirror 104 with respect to the output mirror 103 and forming a resonator structure.

Where the laser medium 102 is irradiated with the excitation light 105 in the apparatus having such a wavelength selection mechanism, the laser medium 102 absorbs the energy of the excitation light 105 and a fluorescence of a characteristic wide wavelength width is generated in the laser medium. When a dielectric reflecting film that reflects actively only a predetermined wavelength, for example, a wavelength close to 750 nm, is formed on the reflecting mirror 104, only the wavelength within a range close to 750 nm is amplified inside the resonator to produce laser oscillation. The output mirror 103, which forms a pair with the reflecting mirror, is an output coupler and induces laser oscillation by reflecting/transmitting the incident light at a fixed ratio. The wavelength of the oscillating laser can be selected by preparing in advance a dielectric antireflective film of a necessary type to be provided on the reflective mirror 104.

In the present configuration, since the reflection characteristic of the dielectric reflecting film formed on the reflecting mirror 104 affects the laser quality, it is possible that the wavelength width will be expanded and the coherence characteristic will decrease. However, since no special element for wavelength selection is inserted into the laser resonance, it is possible to suppress loss inside the resonator and obtain a high output. Furthermore, since the reflecting mirror 104 is controlled uniaxially in wavelength selection, the control mechanism is simple and stable oscillation can be easily obtained with a high positional accuracy of the output mirror. Thus, it is possible to produce a wavelength variable laser that generates high-output oscillations while having a small and simple structure.

First Example

Figure 3:
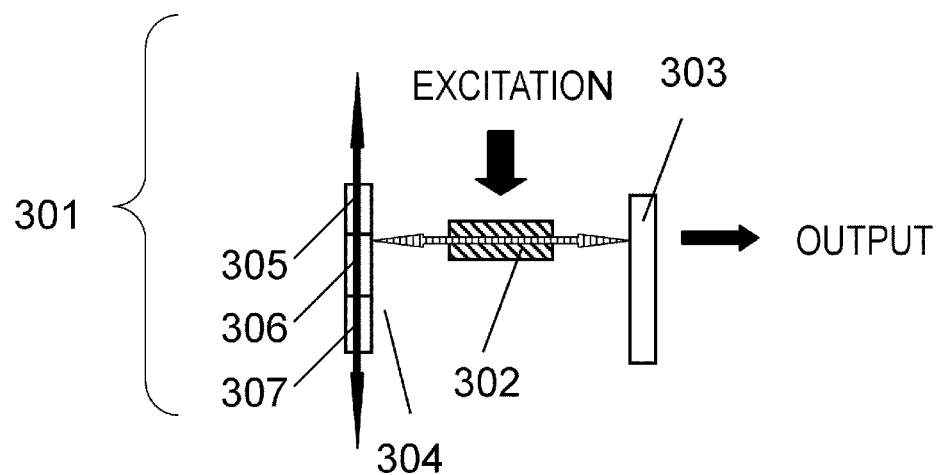
FIG. 3 is a plan view of the laser resonator of the first example.

A laser resonator 301 is shown as a first example in FIG. 3. In this configuration a reflecting mirror 304 and an output mirror 303 are disposed opposite each other. The reflecting mirror includes a high-transmittance portion 305 that has increased transmittance, a region 306 where a dielectric reflecting film A is formed, and a region 307 where another dielectric reflecting film B is formed. The high-reflectance portion 305 is formed by a dielectric antireflection film. In this example, a plurality of (two) reflecting films are used, but the number of reflecting films is not limited to two. An excitation laser light source is used for the excitation of the laser medium. The reflecting mirror 304 inside the resonator shown in FIG. 3 is positionally controlled along one axis as shown by an arrow in the figure. The reflecting mirror corresponds to the reflecting unit in accordance with the present invention. The dielectric reflecting film A and the dielectric reflecting film B correspond to the first plane in accordance with the present invention. The high-transmittance portion corresponds to the second plane in accordance with the present invention. The plane as referred to herein may be a plane to a degree necessary for laser oscillation.

Figure 4:
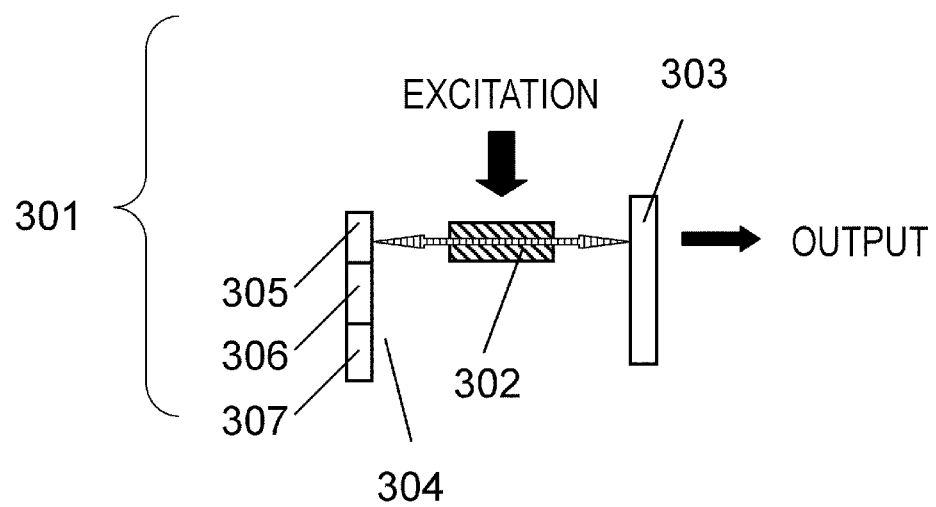
FIG. 4 is a plan view illustrating the non-oscillation state of the laser resonator of the first example.
Figure 5:
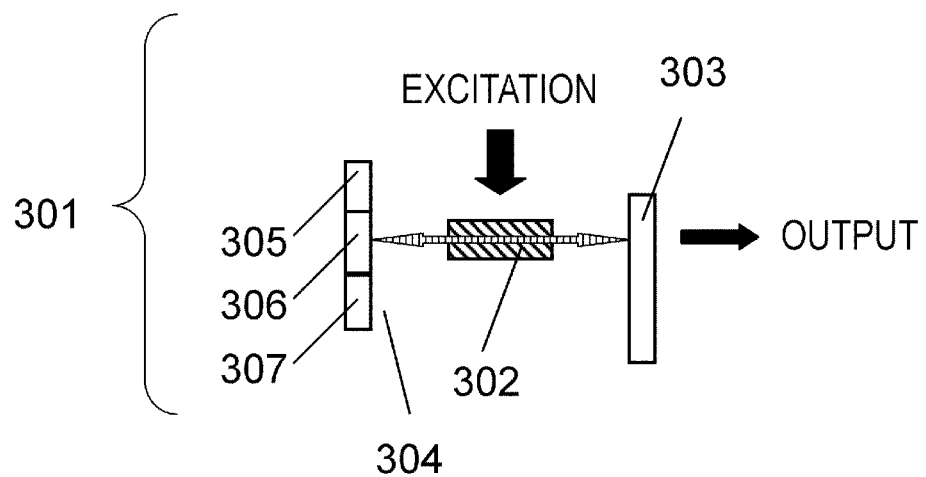
FIG. 5 is a plan view illustrating the oscillation state of the laser resonator of the first example.

FIG. 4 and FIG. 5 show the state of the resonator in the case where the reflecting mirror 304 is moved while being maintained opposite the output mirror 303.

FIG. 4 shows a state in which the position of the reflecting mirror 304 is controlled so that the laser medium 302 is disposed on the line connecting the high-transmittance portion 305 and the output mirror 303. Thus, the high-transmittance portion and the output mirror face each other, with the laser medium being interposed therebetween. In this case, the loss inside the resonator, which is a loss factor other than the loss relating to the output of the output mirror 303, is large and a non-oscillation state is assumed in which the laser oscillation condition is not fulfilled. However, by irradiating the laser radiation with the excitation light, it is possible to obtain a constant temperature of the laser medium in a state in which laser oscillation is not generated. Such a non-oscillation state is a standby state that also serves to warm up the laser medium. By performing the warm-up in the standby state, it is possible to maintain the temperature of the laser medium at a level higher than the predetermined value necessary for stable laser oscillation.

FIG. 5 illustrates the case in which the reflecting mirror 304 is moved so that the region 306 in which the dielectric reflecting film A has been formed and the output mirror 303 form a resonator. Thus, the region 306, in which the dielectric reflecting film A has been formed, and the output mirror 303 face each other, with the laser medium being interposed therebetween. This state is an oscillation state. By using the laser light in the above-described process, it is possible to obtain laser light with stable oscillation and good rise characteristic of the initial state of laser oscillation.

Further, where the reflecting mirror 304 is moved so that the region 307 where the dielectric reflecting film B has been formed and the output mirror 303 form a resonator, wavelength selection becomes possible and the wavelength is determined according to the selected dielectric reflecting film.

A drive unit such as a stepping motor may be provided to obtain a configuration in which the reflecting mirror 304 can be moved between a position in which the non-oscillation state is obtained and the position in which the oscillation film is obtained.

As described hereinabove, in the present configuration, the standby state, which is the non-oscillation state, can be formed by controlling the position of the reflecting mirror in the resonator, that is, even without providing a special wavelength selection mechanism. In accordance with the present invention, the reflected light is not always necessary in the standby state. Therefore, a configuration may be used in which an antireflective film constituted by a dielectric film is formed on the reflecting mirror surface to reduce the unnecessary reflected light.

Second Example

Figure 6:
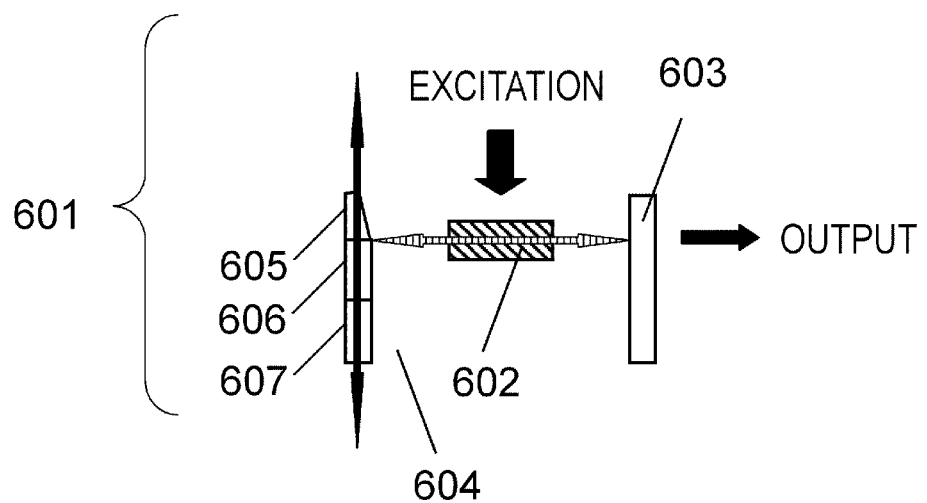
FIG. 6 is a plan view of the laser resonator of the second example.

FIG. 6 shows a laser resonator 601 as a second example. In this configuration a reflecting mirror 604 and an output mirror 603 are disposed opposite each other. The reflecting mirror 604 includes a nonparallel plane portion 605 that is disposed opposite the output mirror 603, a region 606 having formed therein a dielectric reflecting film A that selects the oscillation wavelength in a wavelength range in which laser oscillation can be generated, and a region 607 where another dielectric reflecting film B is formed. In this example, a plurality of (two) reflecting films are used, but the number of reflecting films is not limited to two. An excitation laser light source is used for the excitation of the laser medium. The reflecting mirror 604 inside the resonator shown in FIG. 6 is positionally controlled along one axis as shown by an arrow in the figure. The nonparallel plane portion corresponds to the third plane in accordance with the present invention.

Figure 7:
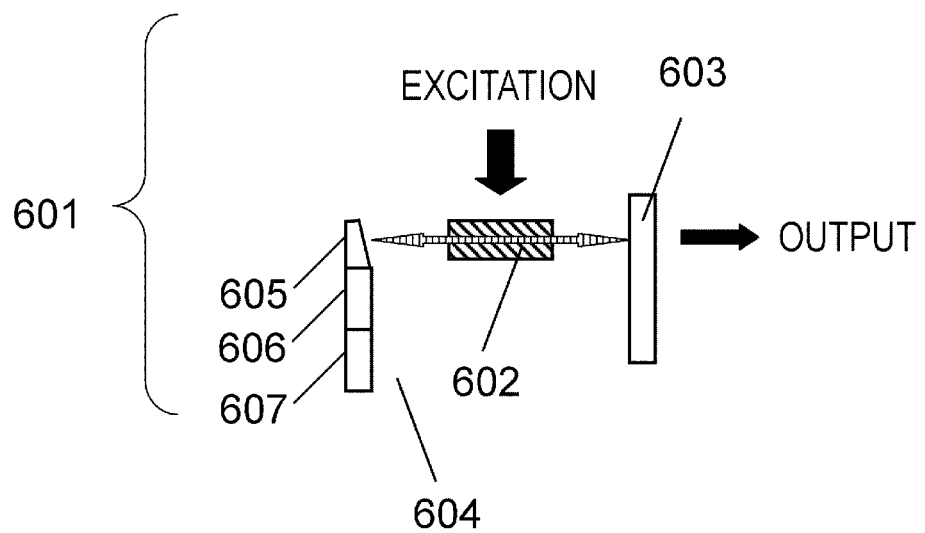
FIG. 7 is a plan view illustrating the non-oscillation state of the laser resonator of the second example.
Figure 8:
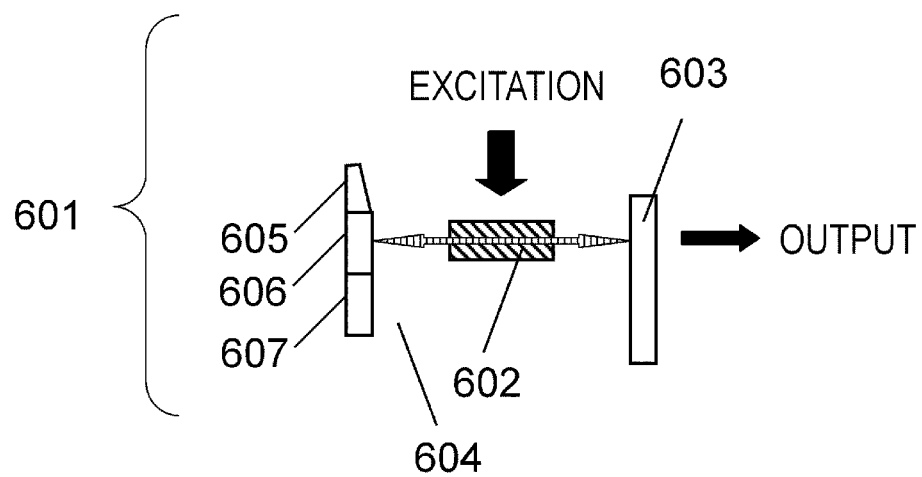
FIG. 8 is a plan view illustrating the oscillation state of the laser resonator of the second example.

FIG. 7 and FIG. 8 show the state of the resonator in the case where the reflecting mirror 604 is moved while causing it to be opposite the output mirror 603.

FIG. 7 shows a state in which the position of the reflecting mirror 604 is controlled so that a laser medium 602 is disposed on the inside of a line connecting the nonparallel plane portion 605 and the output mirror 603. In this case, the loss inside the resonator, which is a loss factor other than the loss relating to the output of the output mirror 603, is large and a non-oscillation state is assumed in which the laser oscillation condition is not fulfilled. However, by irradiating the laser medium with the excitation light, it is possible to obtain a constant temperature of the laser medium in a state in which laser oscillation is not generated. Such a non-oscillation state is a standby state that also serves to warm up the laser medium.

FIG. 8 illustrates the case in which the reflecting mirror 604 is moved so that the region 606 in which the dielectric reflecting film A has been formed and the output mirror 603 form a resonator. This state is an oscillation state. By using the laser light in the above-described process, it is possible to obtain laser light with stable oscillation and good rise characteristic of the initial state of laser oscillation. With such a configuration, similarly to the first example, laser light with stable oscillation and good initial rise characteristic is obtained with a configuration including only basic laser resonator and the reflecting mirror 604 having a wavelength selection mechanism.

Further, wavelength selection becomes possible when the reflecting mirror 604 is moved so that the region 607 where the dielectric reflecting film B has been formed and the output mirror 603 form a resonator.

Variation Example

Figure 9:
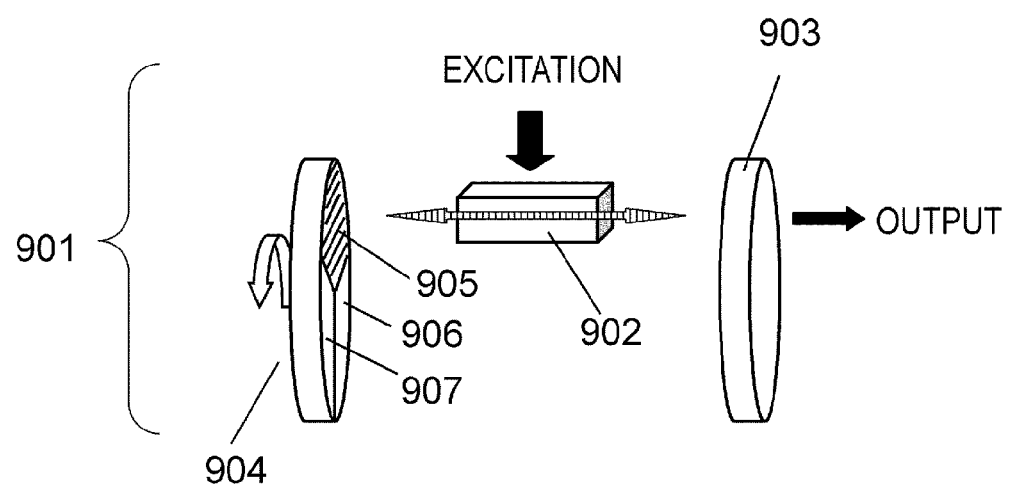
FIG. 9 is a plan view illustrating a laser resonator using a rotating reflecting mirror.

In the example explained hereinbelow, a disk-like flat plate that moves rotationally in a state of facing the output mirror, such as shown in FIG. 9, is explained as a reflecting mirror.

When a flat plate performing a linear motion is used, as in the above-mentioned example, a reflecting film corresponding to the predetermined wavelength is formed orthogonally to the movement direction of the reflecting mirror and a non-oscillation portion is formed at the end of the reflecting mirror. By contrast, when a disk-like flat plate performing a rotation motion is used, the disk-like reflecting mirror is rotated in the center, an output mirror 903 and a reflecting mirror 904 are disposed at mutually opposing positions, and a resonator structure is obtained in which the laser medium is disposed at a position offset from the central axis.

The reflecting mirror 904 is divided into fan-shaped sections, a high-transmittance portion 905 with increased transmission is used in the non-oscillation state, and portions 906 and 907 which are dielectric reflecting film portions are used in the oscillation state. When the high-transmittance portion 905 is used as a resonator, the loss inside the resonator is as large as in Examples 1 and 2 and therefore a non-oscillation state is assumed in which the laser oscillation condition is not fulfilled.

The arrangement of the non-oscillation portion and the reflecting film provided at the reflecting mirror can be selected at random. Thus, the non-oscillation portion may be disposed in the center and the reflecting films for a predetermined wavelength may be configured at both sides. With such a configuration, the laser beams with two necessary wavelengths can be rapidly ON/OFF switched. The reflecting film and the non-oscillation portion can be produced at random and the reflecting mirror can be movably used. In such a case, a random combination of ON/OFF switching and selection of oscillation wavelength can be used, while maintaining the laser output stability.

Third Example

Figure 10:
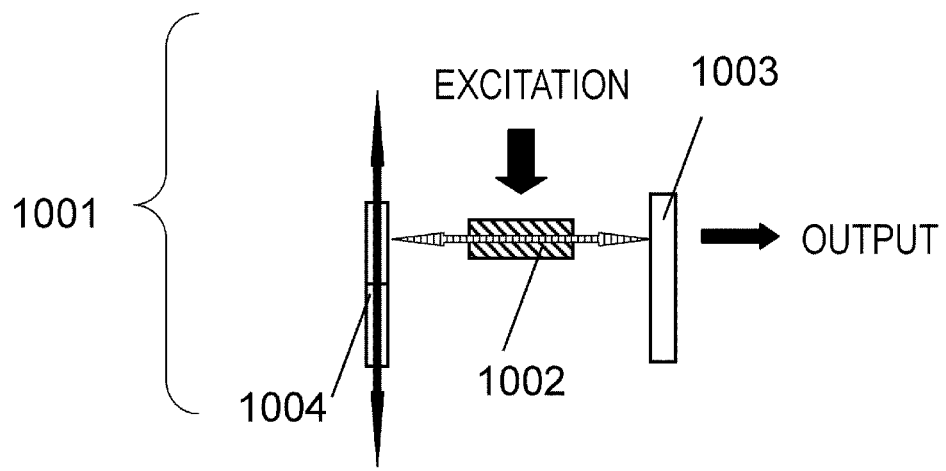
FIG. 10 is a plan view of the laser resonator of the third example.

FIG. 10 shows a laser resonator 1001 as a third example. An excitation laser light source is used for exciting the laser medium. In the resonator configuration, a reflecting mirror 1004 and an output mirror 1003 are disposed opposite each other. The control is performed such that a configuration is obtained in which the control range of the reflecting mirror is expanded and the laser medium is not placed on the orthogonal optical axis connecting the reflecting mirror and the output mirror. In this case, the laser resonator structure collapses, and therefore the laser oscillation condition cannot be fulfilled and laser oscillation cannot be induced. Meanwhile, by irradiating the laser medium with the excitation light, it is possible to maintain a constant temperature of the laser medium in a state without laser oscillation. This configuration includes only a basic laser resonator and the reflecting mirror 1004 having a wavelength selection mechanism, and stable laser light with good initial rise characteristic can be obtained during laser oscillation. The effect obtained with such a configuration is similar to that obtained by installing a shutter mechanism inside the resonator.

Figure 11:
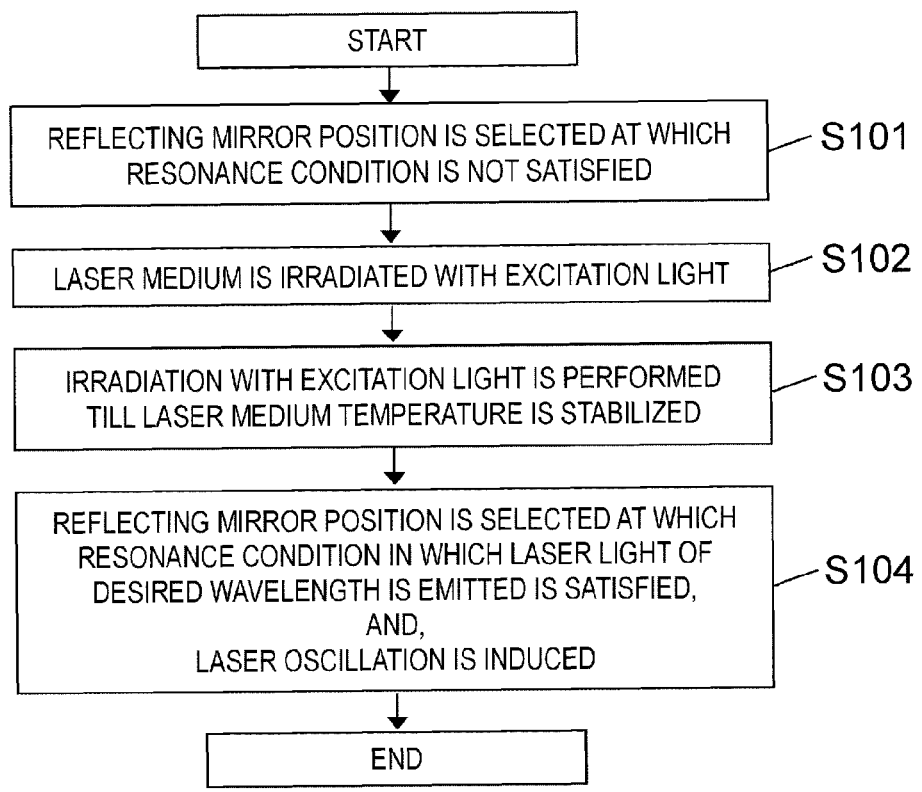
FIG. 11 is a flowchart illustrating a method for controlling a laser apparatus.
Figure 12:
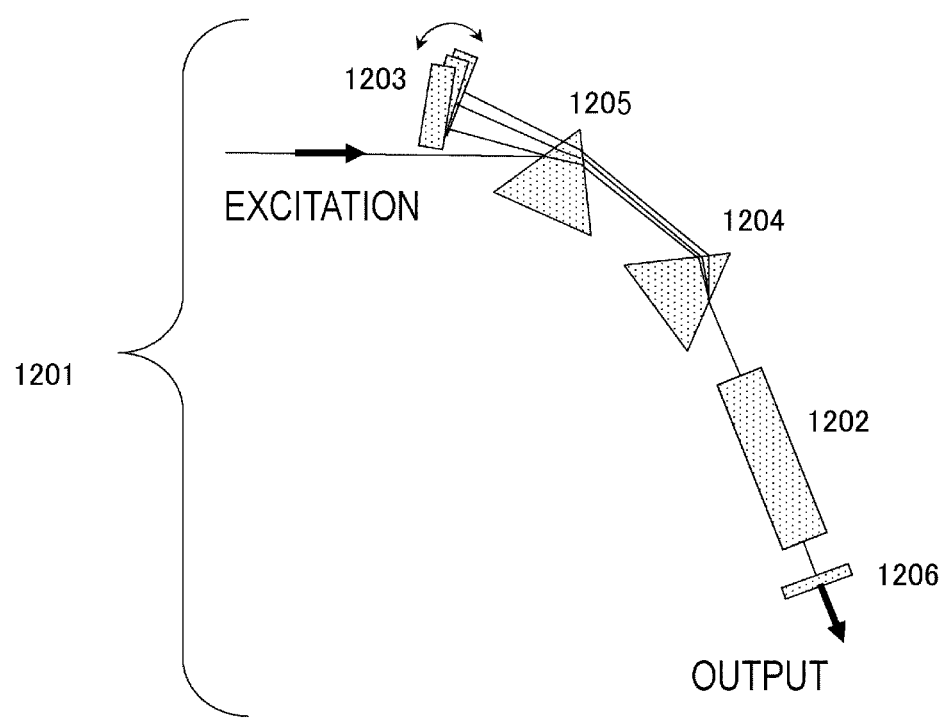
FIG. 12 shows the structure of a laser resonator using the conventional variable wavelength mechanism.

A method for controlling the laser apparatus having the laser resonator configured as in the above-described examples will be explained below with reference to the flowchart shown in FIG. 11. A photoacoustic diagnostic apparatus is used as a specific example of laser apparatus. In this case, the configuration of the first example is explained as a specific example, but this configuration is not limiting.

First, in step S101, a reflecting mirror position is selected at which the resonance condition is not satisfied. In the configuration of the first example, the high-transmittance portion 305 of the reflecting mirror 304 is set opposite the output mirror 303. This state is a non-oscillation state.

In step S102, the laser medium 302 is irradiated with the excitation laser light of the output to be used.

In step S103, this state is maintained and a standby state is assumed. In the present step, the temperature of the laser medium rises and stabilizes. After the present process and selection and setting of the diagnostic site can be performed.

In step S104, the reflecting mirror position is selected to satisfy the resonance condition such that the laser light of a desired wavelength is generated. For this purpose, the position is selected such that a portion of the region 306 where the dialectic reflecting film A has been formed or the region 307 where the dielectric reflecting film B has been formed is used. Laser oscillation is then performed. A laser oscillation state is assumed as a result of the present process, and a photoacoustic signal can be acquired.

With the above-described processing, it is possible to radiate laser light of a desirable wavelength and a constant output.

Fourth Example

The laser apparatuses of the above-described examples can be used in photoacoustic apparatuses using a photoacoustic imaging technique. In photoacoustic imaging, an examination object is irradiated with pulsed light and an acoustic wave (typically, ultrasound wave) generated due to the absorption of the energy of light propagating and diffusing inside the examination object by a light absorbing body is received. Information on the internal portions of the examination object is then converted into an image by using the received signal of the acoustic wave. This technique makes it possible to obtain optical characteristic distribution information, such as the initial pressure generation distribution or light absorption coefficient distribution inside the examination body, as image data.

Figure 13:
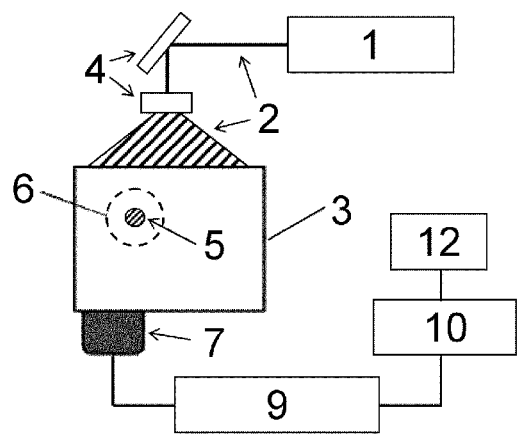
FIG. 13 is a schematic diagram of a photoacoustic measurement device that can use the present invention.

FIG. 13 is a schematic diagram of a photoacoustic apparatus to which the present invention can be applied. The photoacoustic apparatus in accordance with the present invention includes at least the laser apparatus 1 described in any of the aforementioned examples, an acoustic wave detector 7, a signal processing unit 9, and a data processing unit 10. In the present example, a light 2 emitted from the laser apparatus 1 described in any of the aforementioned examples is radiated to an examination object 3 via an optical member 4 such as a lens, a mirror and an optical fiber. Inside the examination object, the irradiated light is absorbed by a light absorbing body 5 (for example, tumor or blood vessel) located inside the examination object, thereby generating an acoustic wave 6. The acoustic wave detector 7 receives the acoustic wave 6, converts the received acoustic wave into an electric signal, and outputs the electric signal to the signal processing unit 9. The signal processing unit 9 performs signal processing, such as A/D conversion or amplification, with respect to the inputted electric signal and outputs the processed signal to the data processing unit 10. The data processing unit 10 generates image data by using the inputted signal and outputs the generated image data to the display unit 12. The display unit 12 displays an image on the basis of the inputted image data.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-87696, filed on Apr. 11, 2011, which is hereby incorporated by reference herein in its entirety.

The invention claimed is:

1. A laser apparatus comprising:
a laser medium;
a light source that radiates light to said laser medium, and excites said laser medium;
a reflecting unit having a first portion that reflects light within a first wavelength range from light generated by excitation of said laser medium and a second portion that reflects light within a second wavelength range from light generated by excitation of said laser medium; and
an output mirror arranged opposite said reflecting unit, with said laser medium being arranged therebetween, causing laser oscillation by inducing resonance of the light within said first wavelength range between said first portion and said output mirror and causing laser oscillation by inducing resonance of the light within said second wavelength range between said second portion and said output mirror,
wherein said reflecting unit and said output mirror constitute a resonator,
wherein said reflecting unit moves in a linear direction so as to switch a first position in which the laser apparatus is set in an oscillation state of the light within said first wavelength range by using said first portion, a second position in which the laser apparatus is set in an oscillation state of the light within said second wavelength range by using said second portion, and a third position in which the laser apparatus is set in a non-oscillation state, said linear direction being a direction intersecting with an arrangement direction of said first portion, said laser medium and said output mirror in a state in which said reflecting unit is in the first position.

2. The laser apparatus according to claim 1, wherein said reflecting unit includes a third portion that transmits the light within said first and second wavelength ranges, and said third portion assumes a position opposite said output mirror in the non-oscillation state.

3. The laser apparatus according to claim 1, wherein said reflecting unit includes a third portion having a plane that is not parallel to said output mirror, and said third plane assumes a position opposite said output mirror in the non-oscillation state.

4. The laser apparatus according claim 1, wherein said first portion and said second portion have respective dielectric reflecting films.

5. The laser apparatus according claim 1, wherein the non-oscillation state is a standby state in which warm-up of said laser medium is performed.

6. The laser apparatus according to claim 1, wherein said linear direction is substantially perpendicular to said direction in which said first portion, said laser medium and said output mirror are arranged in a state in which the laser apparatus is set in an oscillation state of the light within said first wavelength range.

7. A photoacoustic apparatus comprising:
the laser apparatus according claim 1;
an acoustic detector that receives an acoustic wave generated under irradiation of an object by light generated from the laser apparatus and converts the received acoustic wave into an electric signal; and
a data processing unit that uses the electric signal to generate image data.

8. A laser apparatus comprising:
a laser medium;
a light source that radiates light to said laser medium and excites said laser medium;
a reflecting unit having a first portion that reflects light within a first wavelength range from light generated by excitation of said laser medium and a second portion that reflects light within a second wavelength range from light generated by excitation of said laser medium; and
an output mirror arranged opposite said reflecting unit, with said laser medium being arranged therebetween, causing laser oscillation by inducing resonance of the light within said first wavelength range between said first portion and said output mirror and causing laser oscillation by inducing resonance of the light within said second wavelength range between said second portion and said output mirror,
wherein said reflecting unit and said output mirror constitute a resonator, wherein said reflecting unit is rotated around an axis parallel to a direction in which said first portion, said laser medium and said output mirror are arranged in a state in which the laser apparatus is set in an oscillation state of the light within said first wavelength range so as to switch a first position in which the laser apparatus is set in an oscillation state of the light within said first wavelength range by using said first portion, a second position in which the laser apparatus is set in an oscillation state of the light within said second wavelength range by using said second portion, and a third position in which the laser apparatus is set in a non-oscillation state, said axis being parallel to an arrangement direction of said first portion, said laser medium and said output mirror in the state in which said reflecting unit is in the first position.

9. The laser apparatus according to claim 8, wherein said reflecting unit includes a third portion that transmits the light within said first and second wavelength ranges, and said third portion assumes a position opposite said output mirror in the non-oscillation state.

10. The laser apparatus according to claim 8, wherein said reflecting unit includes a third portion having a plane that is not parallel to said output mirror, and said plane assumes a position opposite said output mirror in the non-oscillation state.

11. The laser apparatus according claim 8, wherein said first portion and said second portion have respective dielectric reflecting films.

12. The laser apparatus according claim 8, wherein the non-oscillation state is a standby state in which warm-up of said laser medium is performed.

13. A photoacoustic apparatus comprising:
the laser apparatus according to claim 8;
an acoustic detector that receives an acoustic wave generated under irradiation of an object by light generated from the laser apparatus and converts the received acoustic wave into an electric signal; and
a data processing unit that uses the electric signal to generate image data.

* * * * *